United States Patent
Hodges et al.

(10) Patent No.: US 6,475,360 B1
(45) Date of Patent: Nov. 5, 2002

(54) HEATED ELECTROCHEMICAL CELL

(75) Inventors: Alastair Hodges, San Diego, CA (US); Thomas W. Beck, North Richmond (AU)

(73) Assignee: Lifescan, Inc., Milpitas, CA (US)

( * ) Notice: Subject to any disclaimer, the term of this patent is extended or adjusted under 35 U.S.C. 154(b) by 0 days.

(21) Appl. No.: 09/659,470

(22) Filed: Sep. 11, 2000

Related U.S. Application Data

(63) Continuation of application No. PCT/AU99/00152, filed on Mar. 11, 1999.

(30) Foreign Application Priority Data

Mar. 12, 1998 (AU) ............................................. PR2388

(51) Int. Cl.⁷ ..................... G01N 27/327; G01N 27/333
(52) U.S. Cl. ............. 204/403.14; 204/416; 204/403.01
(58) Field of Search ................................. 204/403, 416, 204/403.01, 403.14; 435/817

(56) References Cited

U.S. PATENT DOCUMENTS

| | | |
|---|---|---|
| 3,616,411 A | 10/1971 | Rudek et al. |
| 4,053,381 A | 10/1977 | Hamblen et al. |
| 4,076,596 A | 2/1978 | Connery et al. |
| 4,100,048 A | 7/1978 | Pompei et al. |
| 4,224,125 A | 9/1980 | Nakamura et al. |
| 4,301,412 A | 11/1981 | Hill et al. |
| 4,301,414 A | 11/1981 | Hill et al. |

(List continued on next page.)

FOREIGN PATENT DOCUMENTS

| | | |
|---|---|---|
| EP | 0 351 892 A2 | 1/1990 |
| EP | 0 400 918 A1 | 12/1990 |
| EP | 0 471 986 B1 | 2/1992 |
| EP | 0 585 933 A2 | 3/1994 |
| EP | 0 741 186 A2 | 11/1996 |
| EP | 0 764 469 A2 | 3/1997 |
| EP | 0 964 059 A2 | 12/1999 |
| GB | 2 069 702 A | 8/1981 |
| GB | 2 215 846 A | 9/1989 |
| JP | 6-174679 * | 6/1994 |
| WO | WO 97/18464 | 5/1997 |

OTHER PUBLICATIONS

International Search Report, PCT/AU99/00152.*
CAPLUS abstract of KAwaguri et al. (JP 02102448).*
Derwent abstract of Kawaguri et al. (JP 02102448).*
JAPIO abstract of Kawaguri et al. (JP 02102448).*
Derwent abstract of Yoshihisa (JP406174679A).*
JAPIO abstract of Yoshihisa (Jp 406174679 A).*
CAPLUS abstract of Yokoyama et al. ("mediated micro-glucose sensors using 2.mu.m platinum electrodes", Electroanalysis (1992), 4(9), 859–64).*

Primary Examiner—T. Tung
Assistant Examiner—Alex Noguerola
(74) Attorney, Agent, or Firm—Knobbe, Martens, Olson & Bear LLP

(57) ABSTRACT

The invention provides a method for determining the concentration of an analyte in a sample comprising the steps of heating the sample and measuring the concentration of the analyte or the concentration of a species representative thereof in the sample at a predetermined point on a reaction profile by means that are substantially independent of temperature. Also provided is an electrochemical cell comprising a spacer pierced by an aperture which defines a cell wall, a first metal electrode on one side of the spacer extending over one side of the aperture, a second metal electrode on the other side of the spacer extending over the side of the aperture opposite the first electrode, means for admitting a sample to the cell volume defined between the electrodes and the cell wall, and means for heating a sample contained within the cell.

27 Claims, 12 Drawing Sheets

U.S. PATENT DOCUMENTS

| | | |
|---|---|---|
| 4,303,887 A | 12/1981 | Hill et al. |
| 4,319,969 A | 3/1982 | Oda et al. |
| 4,374,013 A | 2/1983 | Enfors |
| 4,404,066 A | 9/1983 | Johnson |
| 4,431,004 A | 2/1984 | Bessman et al. |
| 4,431,507 A | 2/1984 | Nankai et al. |
| 4,508,613 A | 4/1985 | Busta et al. |
| 4,517,291 A | 5/1985 | Seago |
| 4,533,440 A | 8/1985 | Kim |
| 4,545,382 A | 10/1985 | Higgins et al. |
| 4,552,840 A | 11/1985 | Riffer |
| 4,654,197 A | 3/1987 | Lilja et al. |
| 4,664,119 A | 5/1987 | Bessman et al. |
| 4,711,245 A | 12/1987 | Higgins et al. |
| 4,790,925 A | 12/1988 | Miller et al. |
| 4,874,501 A | 10/1989 | Christiansen et al. |
| 4,897,173 A | 1/1990 | Nankai et al. |
| 4,900,424 A | 2/1990 | Birth et al. |
| 4,919,770 A | 4/1990 | Preidel et al. |
| 4,935,345 A | 6/1990 | Guilbeau et al. |
| 4,963,815 A | 10/1990 | Hafeman |
| 4,988,429 A | 1/1991 | Matthiessen |
| 5,059,908 A | 10/1991 | Mina |
| 5,064,516 A | 11/1991 | Rupich |
| 5,108,564 A | 4/1992 | Szuminsky et al. |
| 5,120,420 A | 6/1992 | Nankai et al. |
| 5,122,244 A | 6/1992 | Hoenes et al. |
| 5,126,034 A | 6/1992 | Carter et al. |
| 5,128,015 A | 7/1992 | Szuminsky et al. |
| 5,141,868 A | 8/1992 | Shanks et al. |
| 5,185,256 A | 2/1993 | Nankai et al. |
| 5,192,415 A | 3/1993 | Yoshioka et al. |
| 5,229,282 A | 7/1993 | Yoshioka et al. |
| 5,264,103 A | 11/1993 | Yoshioka et al. |
| 5,266,179 A | 11/1993 | Nankai et al. |
| 5,272,087 A | 12/1993 | El Murr et al. |
| 5,312,590 A | 5/1994 | Gunasingham |
| 5,314,605 A | 5/1994 | Matthiessen |
| 5,320,732 A | 6/1994 | Nankai et al. |
| 5,382,346 A | 1/1995 | Uenoyama et al. |
| 5,384,028 A | 1/1995 | Ito |
| 5,385,846 A | 1/1995 | Kuhn et al. |
| 5,393,399 A | 2/1995 | Van den Berg et al. |
| 5,405,511 A | 4/1995 | White et al. |
| 5,413,690 A | 5/1995 | Kost et al. |
| 5,437,999 A | 8/1995 | Diebold et al. |
| 5,508,171 A | 4/1996 | Walling et al. |
| 5,509,410 A | 4/1996 | Hill et al. |
| 5,512,159 A | 4/1996 | Yoshioka et al. |
| 5,518,590 A | 5/1996 | Fang |
| 5,520,787 A | 5/1996 | Hanagan et al. |
| 5,527,446 A | 6/1996 | Kosek et al. |
| 5,567,302 A | 10/1996 | Song et al. |
| 5,607,565 A | 3/1997 | Azarnia et al. |
| 5,620,579 A | 4/1997 | Genshaw et al. |
| 5,628,890 A | 5/1997 | Carter et al. |
| 5,645,709 A | 7/1997 | Birch et al. |
| 5,846,422 A | 12/1998 | Ditter et al. |
| 5,942,102 A | 8/1999 | Hodges et al. |
| 5,997,817 A | 12/1999 | Crismore et al. |
| 6,270,637 B1 * | 8/2001 | Crismore et al. ........... 204/403 |

* cited by examiner

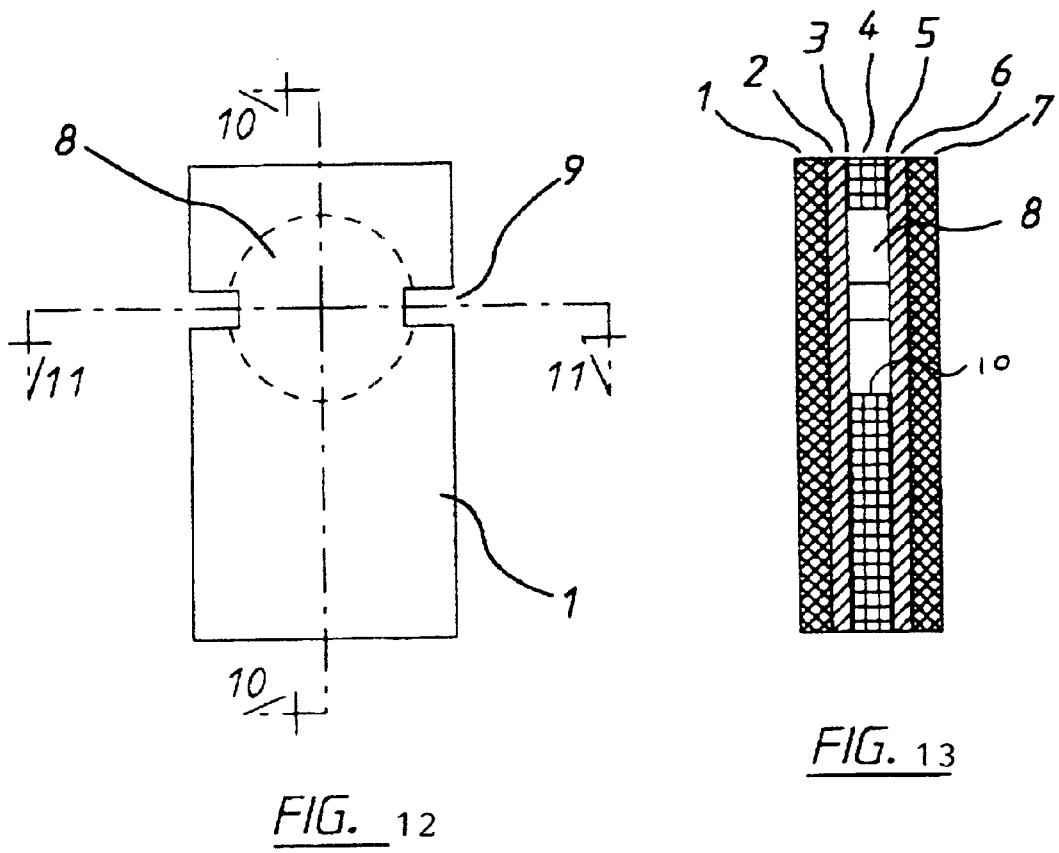
FIG. 12
FIG. 13
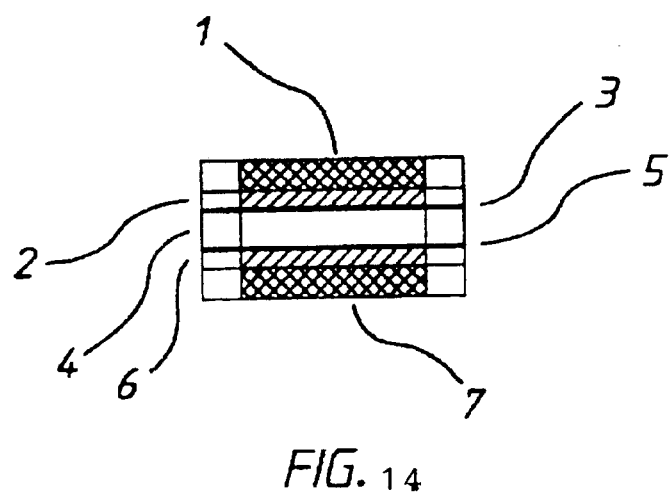
FIG. 14

HEATED ELECTROCHEMICAL CELL

RELATED APPLICATIONS

This application is a continuation, under 35 U.S.C. §120, of copending International Patent Application No. PCT/AU99/00152, filed on Mar. 11, 1999, under the Patent Cooperation Treaty (PCT), which was published by the International Bureau in English on Sep. 16, 1999, which designates the U.S. and claims the benefit of Australian Patent Application No. PP2388, filed on Mar. 12, 1998.

TECHNICAL FIELD

This invention relates to a method and apparatus for measuring the concentration of an analyte in solution.

The invention will be described with particular reference to the measurement of the concentration of glucose in blood but is not limited to that use and has general application for the measurement of analytes other than glucose and for solutions other than blood samples.

BACKGROUND ART

Persons who suffer from diabetes routinely check their blood glucose concentration and there is a need for simple, reliable and inexpensive means to facilitate such routine testing.

In a common method for conducting the tests, a blood sample is combined with an enzyme for example glucose dehydrogenase ("GDH"); the GDH oxidises glucose and in the process becomes reduced. An oxidising mediator, for example ferricyanide, is allowed to react with the reduced GDH returning the GDH to its initial form and producing ferrocyanide in the process. The concentration of ferrocyanide produced is then sensed for example electrochemically or spectroscopically to produce a signal which can be interpreted to give an estimate of the glucose concentration in the sample.

In our co-pending applications PCT/AU96/00723 and PCT/AU96/00724 (the disclosures of which are incorporated herein by reference) there are described methods and apparatus suitable for electrochemically determining the concentration of glucose in blood by electrochemical measurement.

A preferred method for accurately determining the concentration of an analyte is to react all the analyte present in the sample with reagents that produce a species that can be sensed. This requires that the reaction of the analyte go to completion.

For reaction of GDH with glucose to go to substantial completion typically requires several minutes. This is thought to be due to the time required for the glucose to diffuse out from glucose-containing cells of the blood. As this length of time is unacceptably long for the market, it is more usual to measure the glucose concentration over a shorter period, for example 20–30 seconds and accept a less accurate response or apply a factor to estimate the glucose concentration by kinetic extrapolation for example as outlined in co-pending application PCT/AU96/00723. This expedient shortens the time of the test but can lead to loss of precision of the result.

It is an object of the present invention to provide a method and apparatus which avoids or ameliorates the above-discussed deficiencies in the prior art.

DESCRIPTION OF THE INVENTION

According to one aspect the invention consists in a method for determining the concentration of an analyte in a sample comprising the steps of:

heating the sample in a disposable test cell; and
measuring the concentration of the analyte or the concentration of a species representative thereof in the sample at a predetermined point on a reaction profile by means that are substantially independent of the temperature of the sample in the test cell.

Those skilled in the art will understand the term "reaction profile" as used herein to mean the relationship of one reaction variable to another. Often, for example, the reaction profile illustrates the change of concentration of a species with respect to time. Such a profile can provide a skilled addressee with both qualitative and quantitative information, including information as to whether a reaction system has achieved a steady state.

Preferably, the predetermined point on the reaction profile is a steady state, and the species representative of the concentration of the analyte is a mediator, for instance an enzyme mediator.

In one embodiment of the invention the sample is heated by an exothermic reaction produced upon contact of the sample with a suitable reagent or reagents.

In a second embodiment of the invention the sample is heated electrically, for example by means of a current applied to resistive elements associated with the measuring means.

In a highly preferred embodiment the measuring means is an electrochemical cell of the kind described in co-pending applications PCT/AU96/00723 and PCT/AU96/00724 and the sample is heated by application of an alternating voltage signal between electrodes of the sensor.

According to a second aspect the invention consists in an electrochemical cell comprising a spacer pierced by an aperture which defines a cell wall, a first metal electrode on one side of the spacer extending over one side of the aperture, a second metal electrode on the other side of the spacer extending over the side of the aperture opposite the first electrode, means for admitting a sample to the cell volume defined between the electrodes and the cell wall, and means for heating a sample contained within the cell.

BRIEF DESCRIPTION OF THE DRAWINGS

The invention will now be more particularly described by way of example only with reference to the accompanying drawings wherein:

FIG. 12 describes the cell of FIG. 10, which is suitable for use in the method of the preferred embodiments, in plan view (not to scale).

FIG. 13 describes an embodiment of a cell suitable for use in the preferred embodiments in cross-section view on line 10—10 of FIG. 12 (not to scale).

FIG. 14 describes the cell of FIG. 10, which is suitable for use in the method of the preferred embodiments, in end section view (not to scale).

BEST MODE FOR CARRYING OUT THE INVENTION

In preferred embodiments of the method of the invention, glucose concentration is measured using an electrochemical cell of the kind described in PCT/AU96/00723 and/or PCT/AU96/00724 (our co-pending applications). The method of measurement described in those applications utilises an algorithm which enables the value of the diffusion coefficient of the redox mediator to be calculated and the concentration of reduced mediator to be determined in a manner which is substantially independent of sample temperature. The method therein described is different from prior art methods which measure Cottrell current at known times after application of a potential. The present invention differs in that the sample is heated.

In a first embodiment of the present method the blood sample is heated prior to and/or during conduct of the electrochemical measurement by means of an exothermic reaction. In the first embodiment a reagent that liberates heat on contact with blood is contained within the sensor cell. Examples of such reagents are salts which give out heat when they dissolve such as aluminium chloride, lithium halide salts, lithium sulphate, magnesium halide salts and magnesium sulphate. Another class of reagents which would be suitable are those with two components which liberate heat upon mixing. These two components would be placed in separate locations in the sensor during fabrication, for example on coatings upon opposite internal cell walls and are deployed such that when a sample is introduced into the sensor at least one of the components dissolves and then comes into contact with the second component. Upon contact the two components react to liberate heat. The reagents used to generate the heat must not adversely effect the function of the other active elements in the sensor. For instance, they must not corrode the electrode materials, denature an enzyme if present, or adversely interact with any mediator that may be present. Upon introducing a sample of blood into the sensor heat is liberated and the temperature of the blood sample is raised. This facilitates reaction of the glucose with the GDH and since the measurement of ferrocyanide concentration is temperature independent an accurate assessment of glucose concentration can be made in a much shorter time than would otherwise be possible.

Less preferably, the heat generating reagent can be added after the sample is admitted to the cell.

Preferably the sample temperature is raised by from 5 to 15° C., for example from 20° C. to 30° C. or 35° C. within a period of 2 to 10 seconds. The temperature peak is desirably reached within 2–5 seconds.

Figure 1:
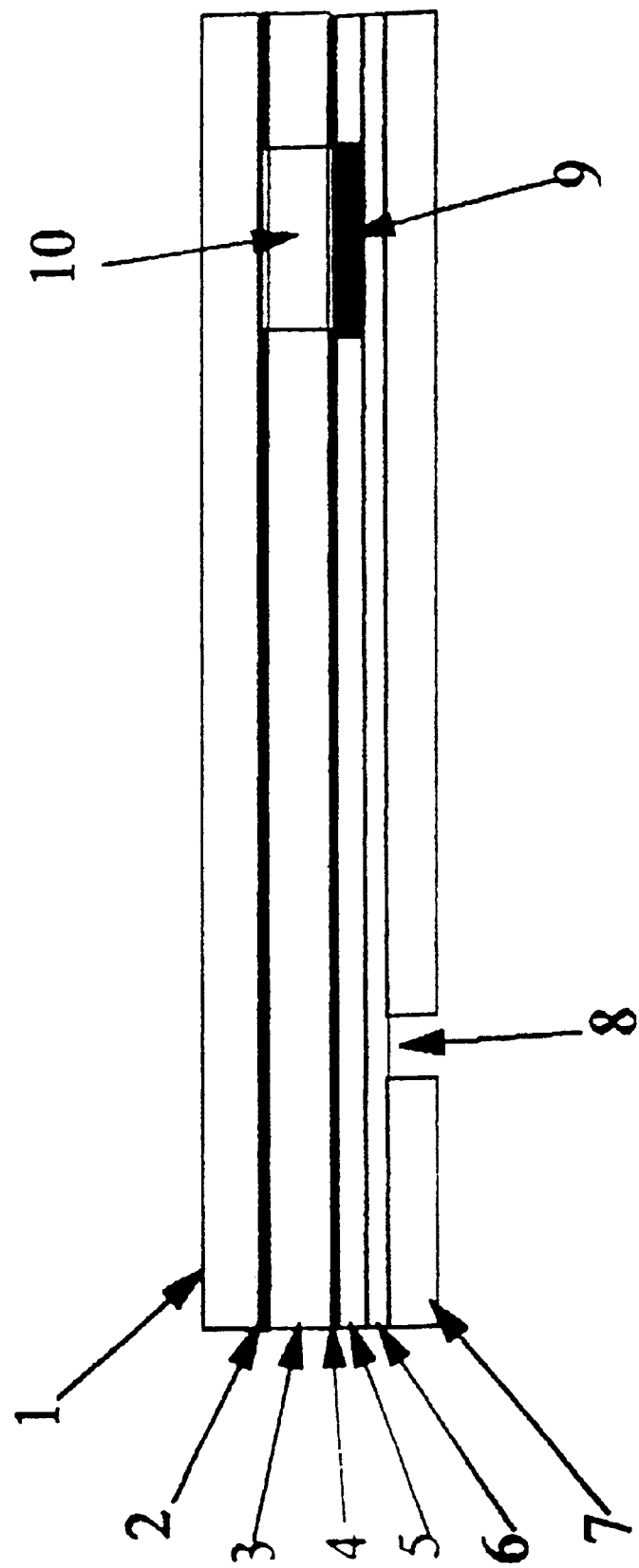
FIG. 1 shows schematically a sensor strip according to the invention in a cross-section taken longitudinally through the midline of the sensor strip.

A second embodiment of the invention employs a cell in which an electrically resistive element is incorporated. The sample may then be electrically heated by passing a current through the resistive element. For example, with reference to FIG. 1 there is shown an electrochemical sensor comprising a plastic substrate 1 bearing a first electrode 2 (for example a sputtered layer of gold), a separator layer 3 having a circular aperture punched out which defines a cell volume 10 bounded on one cylindrical face by first electrode 2. The opposite face of cylindrical cell 10 is covered by a second electrode layer 4 (for example a sputter coating of palladium) which in this case is carried by a rubber or plastic layer 5. A metal foil layer 6 provides electrical contact to a resistive bridge 9 formed in the rubber or plastic layer 5. An insulating layer 7 for example of plastic provides insulation against heat loss through the metal foil. An aperture 8 in layer 7 provides for electrical contact with metal foil layer 6. Resistive bridge 9 is formed for example from carbon particles impregnated into the rubber or plastic of layer 5 at a loading and of a geometry such as to give a suitable electrical resistance between metal foil 6 and electrode layer 4. This method has the advantage of concentrating the heating effect adjacent the cell. Resistive heating elements may be fabricated by other means for example by coating an electrically conducting substrate with an electrically insulating layer which can be made partially conductive in particular regions if desired for example by exposure to particular chemicals and light. When using a cell according to the second embodiment the sample is admitted to the cell, a potential is applied across the resistive element, and after the required amount of heat has been generated the potential across the resistive element is interrupted and after an optional wait time a potential is applied between the first electrode and second electrode to perform the electrochemical assay of the analyte.

Alternatively the potential across the resistive element can be maintained during the assay of the analyte at its initial level or at a lower level sufficient to substantially maintain the sample temperature at the desired level.

In another embodiment, the means for applying the potential to the resistive element is such that the current flowing through the resistive element is monitored and the potential automatically adjusted so as to maintain the required power output. This heats the sample in a reproducible fashion, even if the resistance of the resistive element varies from one sensor to the next. Furthermore, the power level required can be adjusted on the basis of the ambient temperature measured by a separate sensor. The leads to a more reproducible sample temperature being reached over a range of ambient temperature at which the sensor is being used.

In a third embodiment of the invention the sample is heated simply by applying an alternating voltage signal between the working and counter-electrodes of a sensor, for example, of the kind described in our co-pending applications. If this alternating voltage signal has a correct frequency and amplitude it will heat the sample while still allowing an accurate determination of the analyte to be subsequently made by the sensor. Because the voltage signal is alternating any reaction that occurs during one half voltage cycle is reversed during the second half of that cycle, resulting in no net change but in the dissipation of energy that will appear as heat in the sample. This is particularly applicable to sensors of the type disclosed in our abovementioned co-pending patent applications where any small changes that may occur in the cell are quickly removed after interruption of the alternating potential as the cell relaxes back to its initial stage.

When using cells such as described in our co-pending applications (see, e.g., FIGS. 12, 13, and 14), the sample volumes are very small and heating can be achieved with low energy input.

It is known to measure the concentration of a component to be analysed in an aqueous liquid sample by placing the sample into a reaction zone in an electrochemical cell comprising two electrodes having an impedance which renders them suitable for amperometric measurement, The component to be analysed is allowed to react directly with an electrode, or directly or indirectly with a redox reagent whereby to form an oxidisable (or reducible) substance in an amount corresponding to the concentration of the component to be analysed. The quantity of the oxidisable (or reducible) substance present is then estimated electrochemically. Generally this method requires sufficient separation of the electrodes so that electrolysis products at one electrode cannot reach the other electrode and interfere with the processes at the other electrode during the period of measurement.

In PCT/AU96/00365 is described a novel method for determining the concentration of the reduced (or oxidised) form of a redox species in an electrochemical cell of the kind comprising a working electrode and a counter (or counter/reference) electrode spaced from the working electrode. The method involves applying an electrical potential difference between the electrodes, spacing the working electrode from the counter electrode so that reaction products from the counter electrode arrive at the working electrode and selecting the potential of the working electrode so that the rate of electro-oxidation of the reduced form of the species (or of electro-reduction of the oxidised form) is diffusion controlled. By determining the current as a function of time after application of the potential and prior to achievement of a steady state current and then estimating the magnitude of the steady state current, the method previously described allows the diffusion coefficient and/or the concentration of the reduced (oxidised) form of the species to be estimated.

PCT/AU96/00365 exemplifies this method with reference to use of a "thin layer" cell employing a GOD/Ferrocyanide system. As herein used, the term "thin layer electrochemical cell" refers to a cell having closely spaced electrodes such that reaction products from the counter electrode arrive at the working electrode, in practice, the separation of electrodes in such a cell for measuring glucose in blood will be less than 500 microns, and preferably less than 200 microns.

The chemistry used in the exemplified electrochemical cell is as follows:

glucose+GOD→gluconic acid+GOD* reaction 1

GOD*+2 ferricyanide→GOD+2 ferrocyanide reaction 2 where GOD is the enzyme glucose oxidase and GOD* is the 'activated' enzyme. Ferricyanide ($[Fe(CN)_6]^{3-}$) is the 'mediator' which returns the GOD* to its catalytic state. GOD, an enzyme catalyst, is not consumed during the reaction so long as excess mediator is present. Ferrocyanide ($[Fe(CN)_6]^{4-}$) is the product of the total reaction.

Ideally there is initially no ferrocyanide, although in practice there is often a small quantity. After reaction is complete the concentration of ferrocyanide (measured electrochemically) indicates the initial concentration of glucose. The total reaction is the sum of reactions 1 and 2:

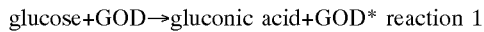
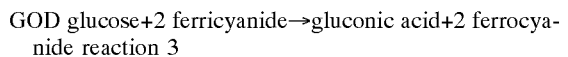

GOD glucose+2 ferricyanide→gluconic acid+2 ferrocyanide reaction 3

"Glucose" refers specifically to β-D-glucose.

The prior art suffers from a number of disadvantages. Firstly, sample size required is greater than desirable. It would be generally preferable to be able to make measurements on samples of reduced volume since this in turn enables use of less invasive methods to obtain samples.

Secondly, it would be generally desirable to the accuracy of measurement and to eliminate or reduce variations due, for example, to cell asymmetry or other factors introduced during mass production of microcells.

Thirdly, it would be generally desirable to reduce the time that is required in which to obtain a measurement. The test protocols used in current commercially available electrochemical glucose sensors involve a predetermined wait period at the beginning of the test during which the enzyme reacts with the glucose to produce the specie that is sensed electrochemically. This initial period is fixed at the maximum necessary to achieve the desired reaction under all conditions of use.

Fourthly, it would be desirable to eliminate variations due to oxygen. Oxygen can be plentiful in blood, either dissolved in the plasma, or bound in hemoglobin. It can also be introduced during "finger sticking," where a blood drop of small volume and high surface area is exposed to the atmosphere prior to introduction to a cell. Oxygen can interfere since oxygen is a mediator for GOD. The reaction is as follows:

glucose+GOD→gluconic acid+GOD* reaction 4

GOD*+oxygen+water→GOD+hydrogen peroxide reaction 5

The total reaction is given by:

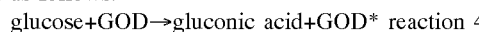
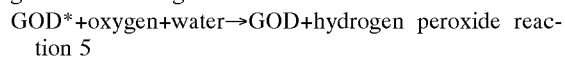
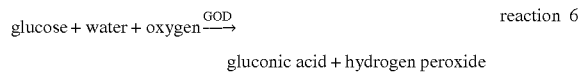

reaction 6

In most situations the complication of oxygen also acting as a mediator is unwanted simply because the concentration of final ferrocyanide no longer is directly proportional to the concentration of initial glucose. Instead, the initial glucose concentration is then related to both the final concentration of ferrocyanide and of hydrogen peroxide.

A method is provided for determining the concentration of a reduced (or oxidised) form of a redox species in an electrochemical cell of the kind comprising a working electrode and a counter electrode spaced from the working electrode by a predetermined distance, said method comprising the steps of:

(a) applying an electric potential between the electrodes, wherein the electrodes are spaced so that reaction products from the counter electrode arrive at the such that the rate of the electro-oxidation of the reduced form (or oxidised form) of the redox species is diffusion controlled, (b) determining current as a function of time after application of the potential and prior to achievement of a steady state current, (c) estimating the magnitude of the steady state current, (d) interrupting, or reversing the polarity, of the potential, (e) repeating step (b) and step (c).

It was discovered that if the polarity is reversed (i.e., the anode becomes the cathode and vice versa) after the initial steady state current is achieved, then a second transient current can be observed and after a period of time a second steady state is achieved. This has proved useful for diagnosing, and for reducing the effects of, cell asymmetry and other factors which influence the transient current. It also permits greater reliability and/or accuracy of estimation by allowing measurements to be made repetitively using reverse polarities. Likewise, if the potential is interrupted for a time sufficient for the concentration profile to relax to a random state and is then reapplied, steps (b) and (c) can be repeated.

A method is provided for measuring the concentration of glucose in a sample by means of a cell having a working electrode, a counter electrode, an enzyme catalyst, and a redox mediator, comprising the steps of operating the cell at a potential higher than that of the redox reaction so as to oxidise hydrogen peroxide at the anode and then conducting a method as described above.

By this means the interference of oxygen can be ameliorated as explained in more detail hereinafter.

A method is provided wherein the sample is allowed to react with an enzyme catalyst and a redox mediator comprising the steps of:

(a) applying a potential between the electrodes before or during filling of the cell, (b) measuring the increase in current as a function of time, (c) determining or predicting from the measurement in step (b) the time of completion of reaction with said catalyst, and (d) then interrupting or reversing the polarity of the potential.

An electrochemical cell suitable for use in preferred embodiments is depicted schematically (not to scale) in FIGS. 12, 13, and 14. The cell comprises a polyester core 4 approximately 18 mm×5 mm and 100 micron thick and having a circular aperture 8 of 3.4 mm diameter. Aperture 8 defines a cylindrical cell side wall 10. Adhered to one side of core 4 is a polyester sheet 1 having a sputter coating of palladium 2. The sputter coating took place at between 4 and 6 millibar pressure in an atmosphere of argon gas to give a uniform coating thickness of 100–1000 angstroms. The sheet is adhered by means of an adhesive 3 to core 4 with palladium 2 adjacent core 4 and covering aperture 8.

A second polyester sheet 7 having a second sputter coating of palladium 6 is adhered by means of contact adhesive 5 to the other side of core 4 and covering aperture 8. There is thereby defined a cell having cylindrical side wall 10 and closed each end by palladium metal. The assembly is notched at 9 to provide for a solution to be admitted to the cell or to be drawn in by wicking or capillary action and to allow air to escape.

The metal films 2, 6 are connected with suitable electrical connections or formations whereby potentials may be applied and currently measured. The cell is furnished with GOD and ferrocyanide in dry form.

In use according to the method a drop of blood is drawn into the cell at 9 by capillary action and allowed to react.

Figure 4:
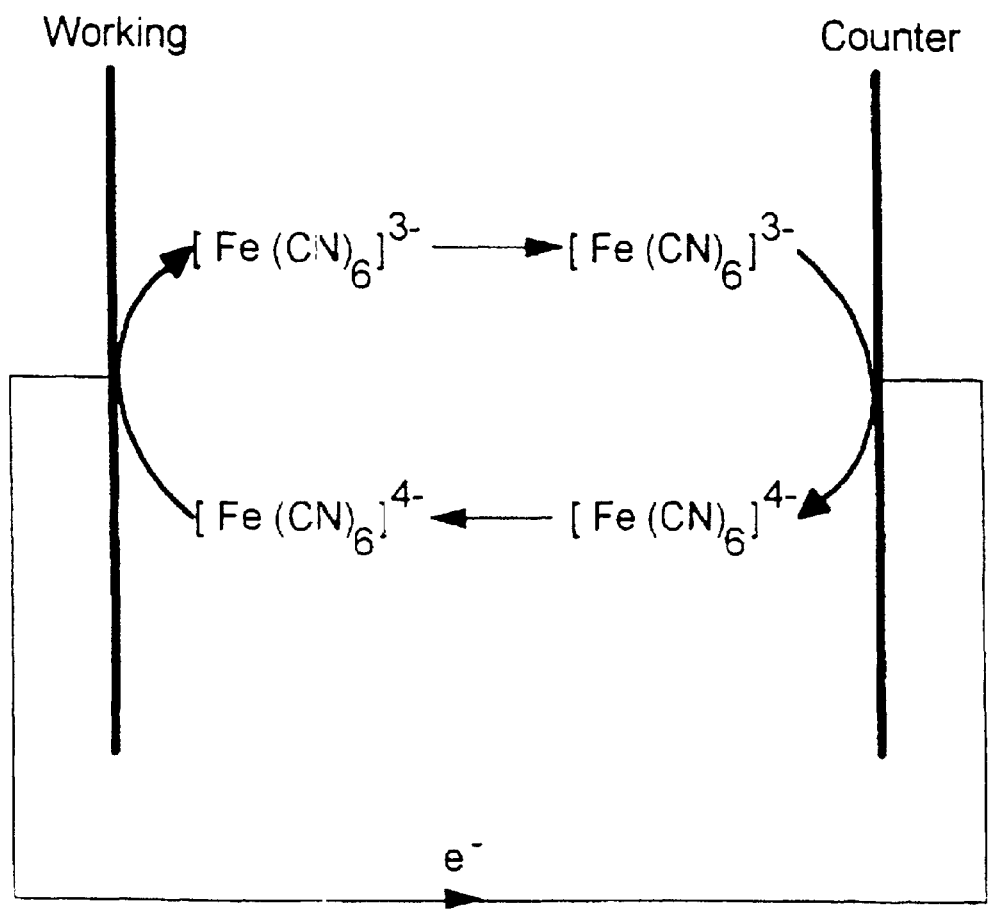
FIG. 4 exemplifies the reactions taking place in a cell according to preferred embodiments.

The electrochemical means for measuring the ferrocyanide concentration after complete reaction can be considered by reference to FIG. 4.

Figure 5:
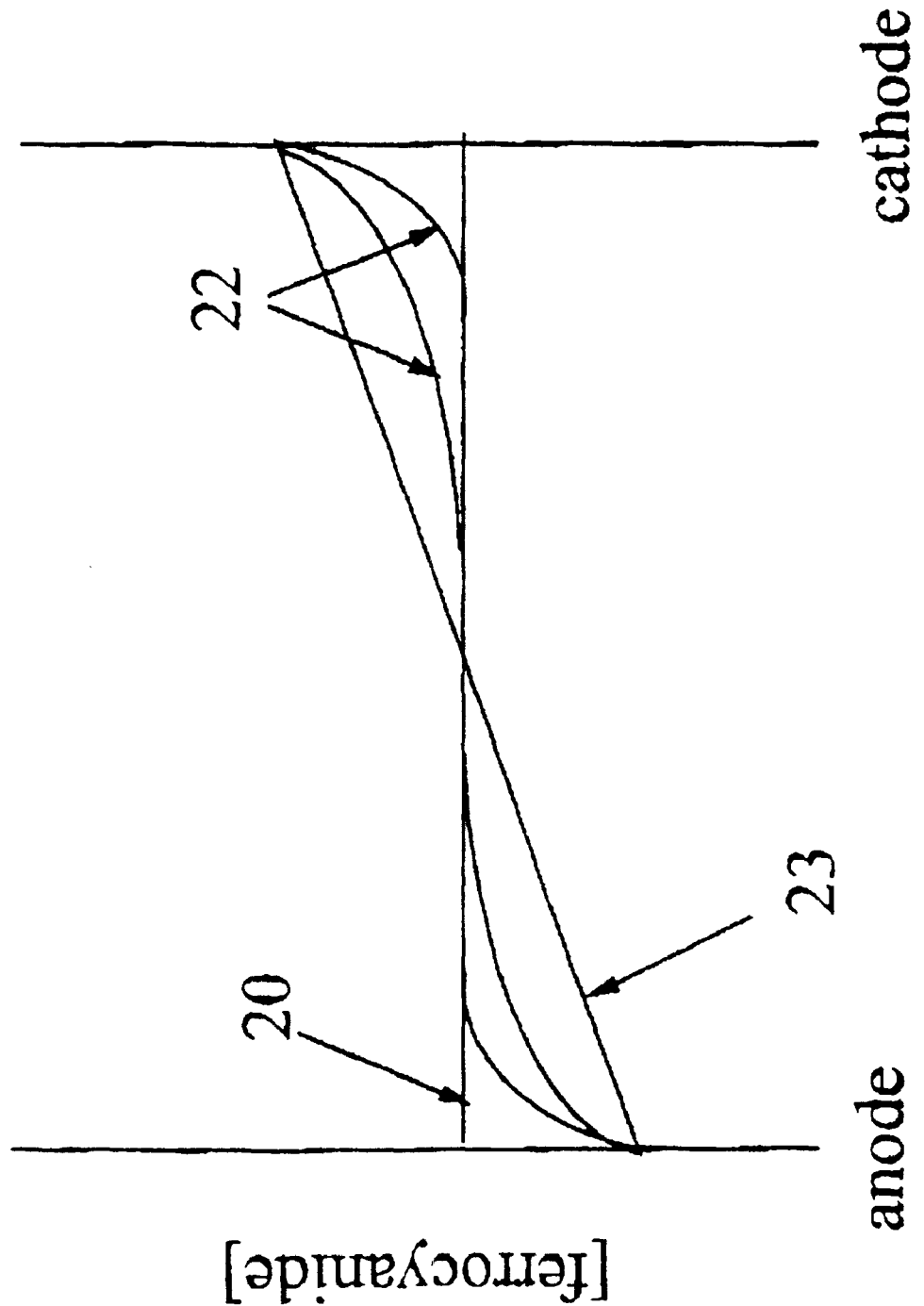
FIG. 5 illustrates the concentration profiles across an electrochemical cell according to the preferred embodiments before the application of an electrical potential, after application of the potential and prior to reaching steady state, and at steady state.

In a thin layer cell the initial concentration of ferrocyanide and ferricyanide (after 'enzymatic' reaction is complete) is equal throughout the cell (the axis of interest being that between the electrodes). The concentration profile of ferrocyanide is given in FIG. 5.

When a particular potential is applied across the cell ferricyanide is converted to ferrocyanide at the cathode and ferrocyanide is converted to ferricyanide at the anode.

The chemistry is so arranged that after complete reaction there is still an excess of ferricyanide compared to ferrocyanide. For this reason the process that limits the complete electrochemical process is the conversion of ferrocyanide to ferricyanide at the anode, simply because ferrocyanide is at a significantly lower concentration. Further the rate limiting step for the reaction of ferrocyanide is the diffusion of ferrocyanide to the anode. After a period of time a steady-state is achieved, wherein the concentration profile of ferrocyanide and ferricyanide remains constant (see FIG. 5).

Therefore there are two limiting situations: initially 20 the ferrocyanide is evenly distributed throughout the cell. Then after a known potential is applied across the cell for a period of time a steady-state concentration profile of ferrocyanide is achieved. The 'transient' 22 reflects the measured cur-rent across the cell as the concentration adjusts from the initial situation to the final steady state situation 23. This is shown as a function of time in FIG. 6. It has been found that the change in the current with time during this 'transient' period is dependent upon the total concentration of ferrocyanide and the diffusion coefficient of ferrocyanide.

By solving the diffusion equations for this situation, it can be shown that the transient can be adequately described by the following equation over a restricted calculable time range.

$$\ln \frac{(i-1)}{i_s} = \frac{-4\pi^2 Dt}{L^2} + \ln(2) \qquad \text{Eqn 1}$$

where $i$ is the measured current, $i_s$ is the current at steady-state, $D$ the diffusion coefficient of ferrocyanide in the cell, $L$ the separation distance between the anode and cathode, and $t$ is time.

This is a simple solution of the general diffusion equation. However, it may be possible to use other solutions.

The final current at steady state also depends upon the total concentration of ferrocyanide and the diffusion coefficient of ferrocyanide. The steady state current can also be modeled by diffusion theory and is given by:

$$i_{ss} = \frac{2DFCA}{L} \qquad \text{Eqn 2}$$

where $F$ is the Faraday constant, $C$ the initial concentration of ferrocyanide, and $A$ the area of the working electrode. By initial concentration is meant the unperturbed concentration (shown as 20 in FIG. 5).

Analysis of the current observed during the transient and also at steady state allows calculation of both the concentration and diffusion coefficient of ferrocyanide, and thus also the initial glucose concentration.

This analysis is achieved by plotting:

$$\ln(i-1)=i_s \qquad \text{Eqn 3}$$

versus time which is substantially linear over a restricted and calculable time range and thus can be analysed for example by linear least squares regression. Since $L$ is a constant for a given cell, measurement of $i$ as a function of time and of $i_{ss}$ thus enables the value of the diffusion coefficient of the redox mediator to be calculated and the concentration of the analyte to be determined.

Another possible way to analyse the data is to use the variation of current with time soon after the potential step is applied to the electrodes. In this time period the current can be adequately described by the Cottrell equation. That is:

$$i = FAD^{1/2}C/(pi^{1/2}t^{1/2}) \qquad \text{Eqn 4}$$

By least squares regression on a plot of $i$ versus $1/t^{1/2}$ a value of $FAD^{1/2}C/pi^{1/2}$ can be estimated from the slope of this plot. The steady state current $i_{ss}$ is given as before, so by combining the slope of the plot given above with the steady state current a value of the concentration of the ferrocyanide, independent of the diffusion coefficient of the ferrocyanide in the cell can be estimated. This is given by:

$$C = 2\text{slope}^2 \text{pi}/(FALi_{ss}) \quad \text{Eqn 5}$$

Figure 6:
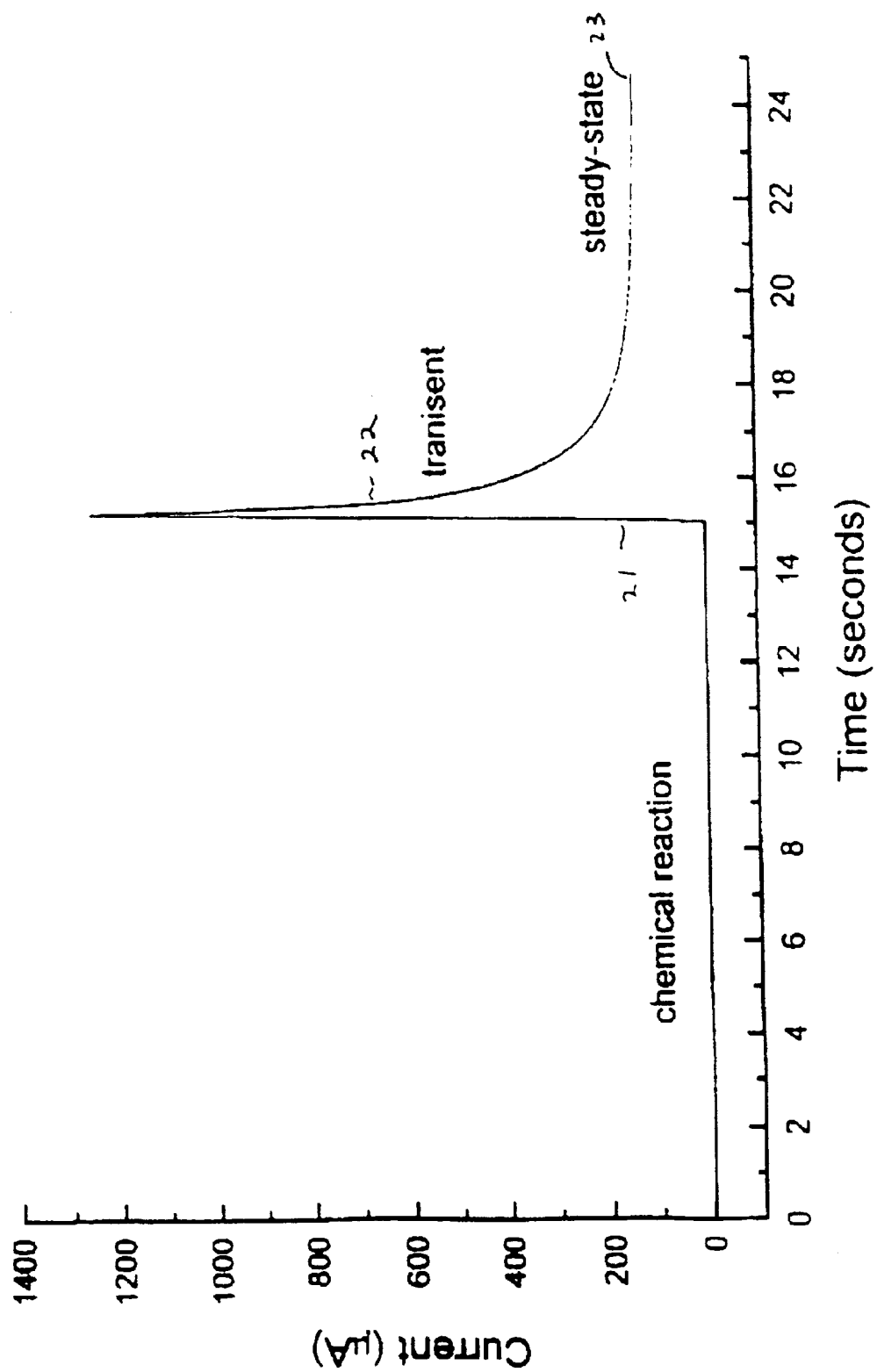
FIG. 6 shows the time dependence of current prior to and after application of electrical potential.

In an example according to the preferred embodiments, a sample of blood is admitted to a thin layer cell containing a GOD/ferrocyanide system such as previously described with reference to FIGS. 12, 13, and 14. As illustrated in FIG. 6, after allowing a short time 20 for reaction, an electric potential is applied between the electrodes, current flow commences when the potential is applied 21 but then falls as a transient 22 towards a steady state level 23. The diffusion coefficient and/or glucose concentration are derived by measuring current as a function of time and by estimating the steady state current.

Figure 7:
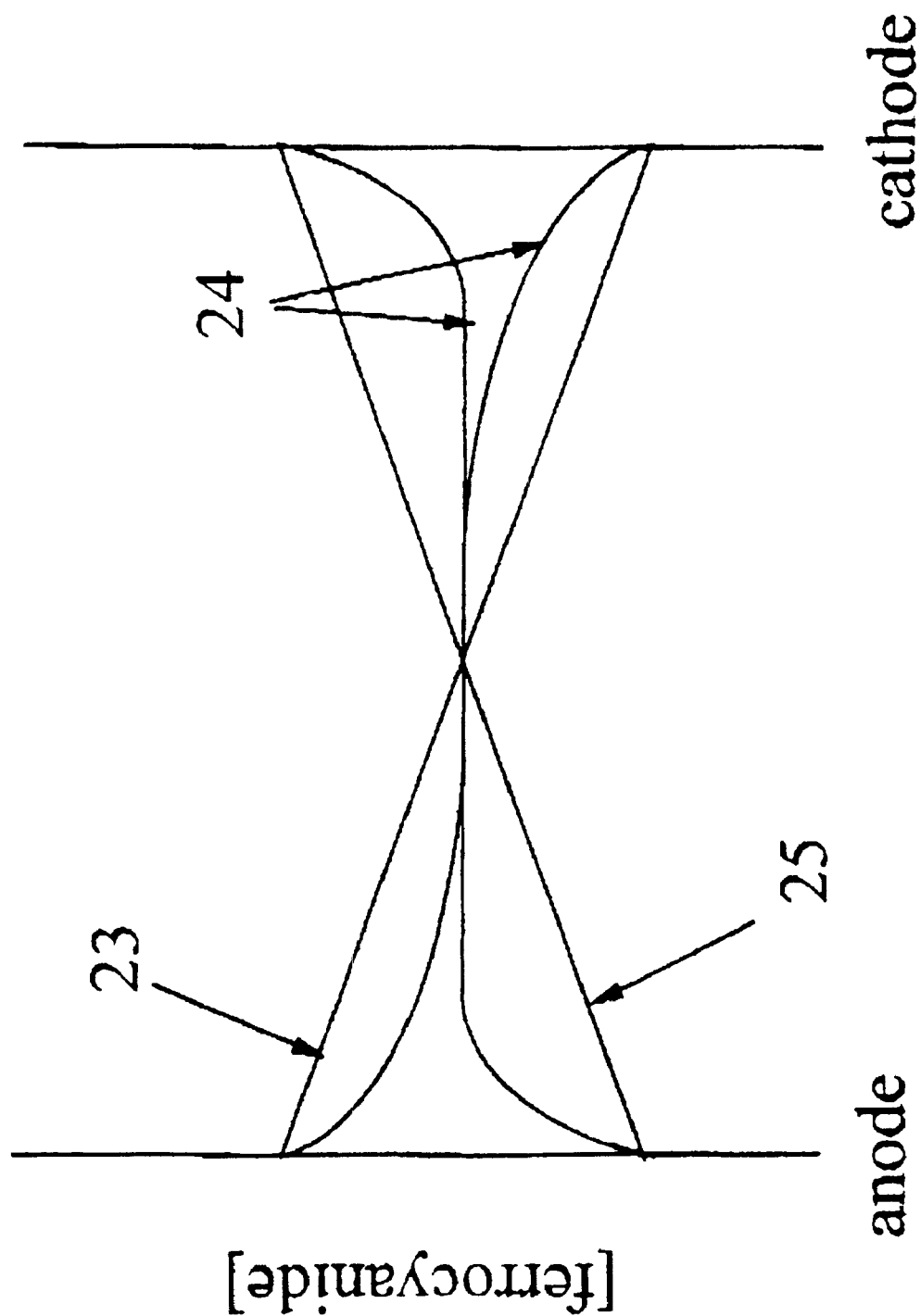
FIG. 7 shows the ferrocyanide concentration profiles across an electrochemical cell according to the preferred embodiments prior to a polarity reversal, after reversal and prior to reaching a steady state, and at steady state.
Figure 8:
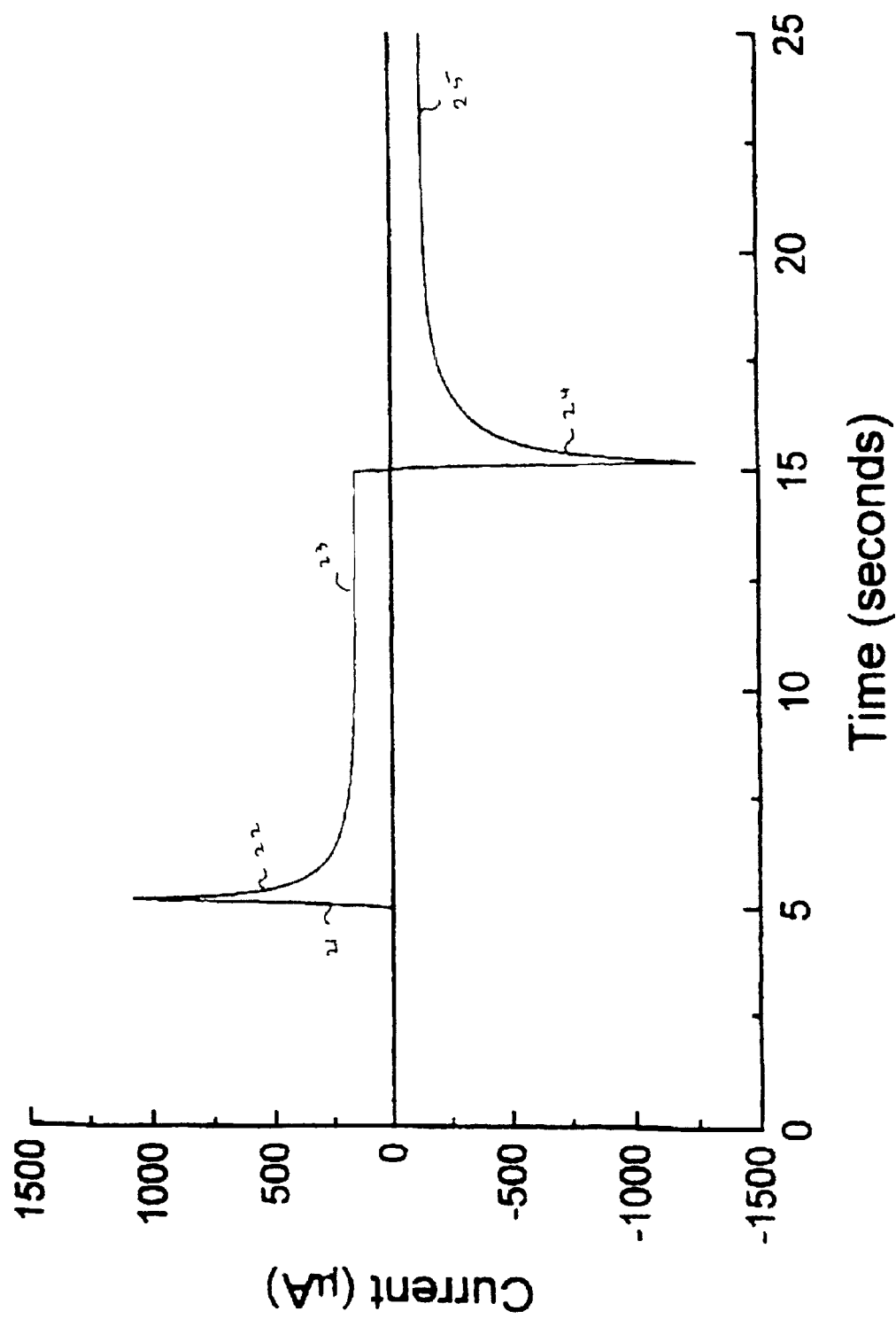
FIG. 8 shows the time dependence of current prior to and after a polarity reversal.

According to the preferred embodiments, the current is then interrupted, or reversed in polarity, for example by means of a suitable switch. If the polarity is reversed, a second transient is then observed, and a second steady, state is reached after a further period of time although the profile is reversed. The underlying change in ferrocyanide concentration profile across the cell is shown schematically in FIG. 7. The initial concentration profile prior to current reversal is 23. The new steady state concentration profile is shown at 25. The transient concentration profiles are exemplified at 24.

By solving the diffusion equations for this situation, it can be shown that the transient current is described by.

$$\ln \frac{(i-1)}{i_s} = \frac{-4\pi^2 Dt}{L^2} + \ln(4) \quad \text{Eqn 6}$$

It is therefore simple to re-estimate the diffusion coefficient and concentration under the reversed polarity conditions. In theory the results should be independent of the type of transient or polarity. In practice, the results may differ due to factors affecting the transient such as sample inhomogeneity, state of the electrodes, or more importantly, due to asymmetries in the cell construction. This measure is therefore useful for cell diagnosis and also enables greater accuracy by allowing repetitive measurement and averaging with reverse polarities.

Figure 9:
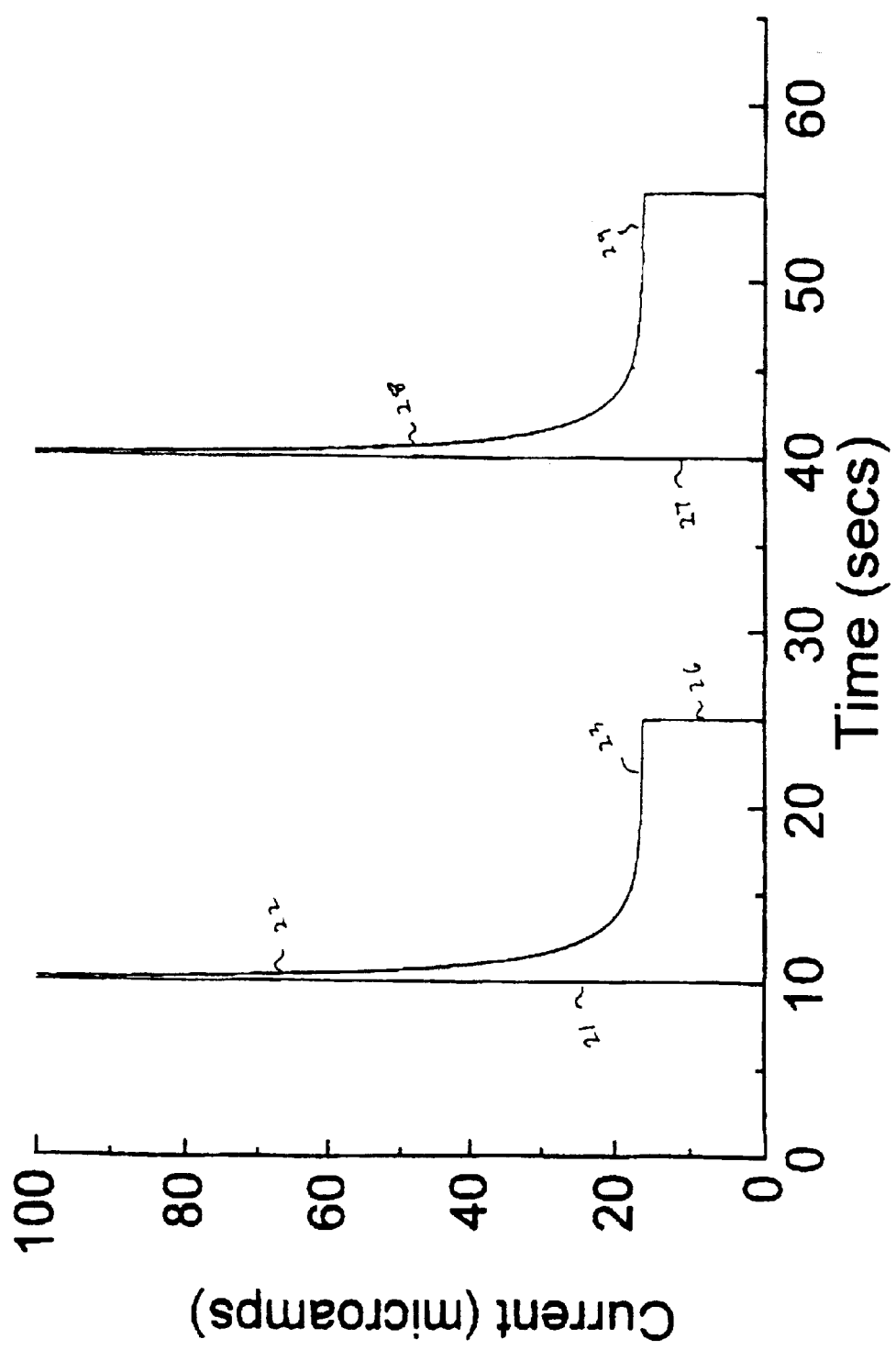
FIG. 9 shows the time dependence of current prior to and after an interruption of applied potential of 15 seconds.

Similarly, if the potential is interrupted after steady state is reached, the initial concentration profile will be re-established in a short time (for example 4 seconds). Once the initial state is re-established (or approximated) the potential can be re-applied and the procedure repeated without current reversal. FIG. 9 shows a plot of current versus time similar to that of FIG. 6 but having the potential interrupted at 26 and reapplied after 15 seconds at 27 yielding a new transient current 28 and then a state 29.

Figure 10:
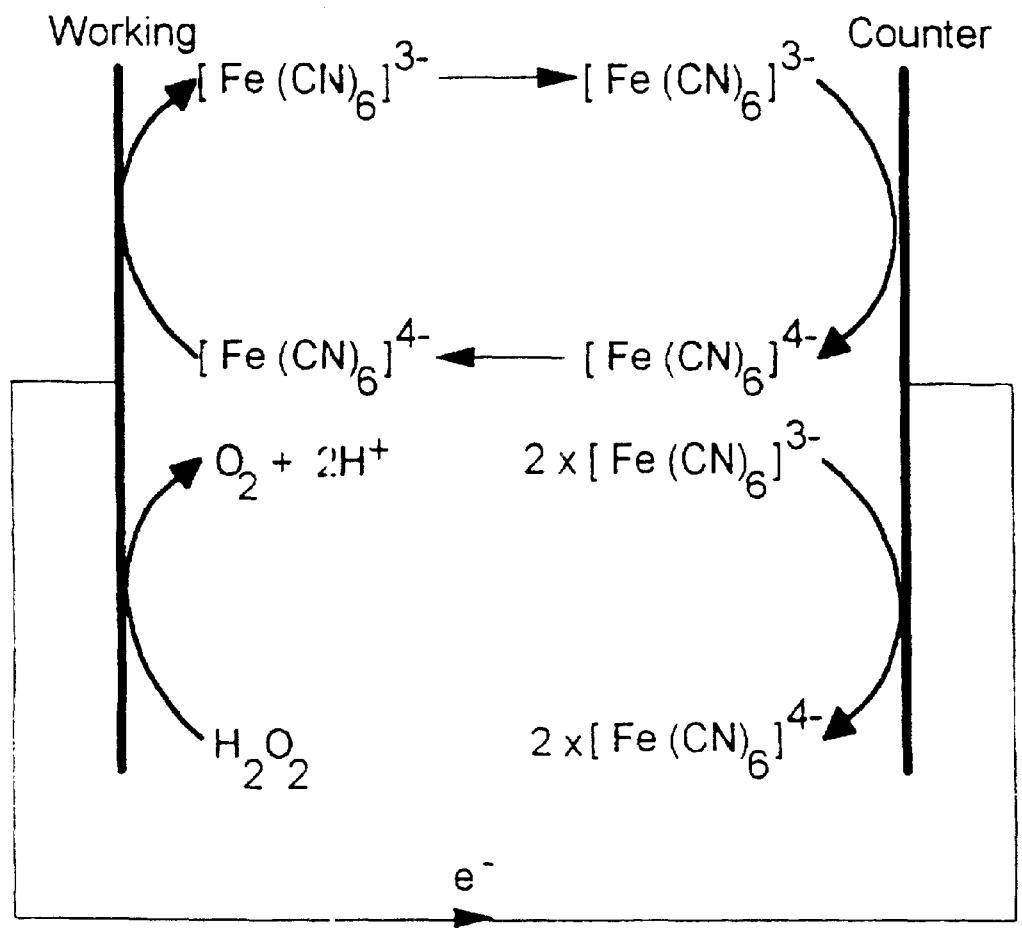
FIG. 10 shows the reactions in an electrochemical cell with peroxide oxidation.

As stated previously, the presence of oxygen in the blood is an interference since the concentration of final ferrocyanide is then not directly proportional to the initial glucose. Instead the initial glucose is related both to the final concentration of ferrocyanide plus hydrogen peroxide. However, it was found that hydrogen peroxide can be oxidised at the anode at a known potential which is higher than that for the ferrocyanide/ferricyanide redox reaction. The total electrochemical path is given in FIG. 10. The hydrogen peroxide reaction is:

hydrogen peroxide→oxygen+2H$^+$+2 e$^-$ reaction 7

Figure 11:
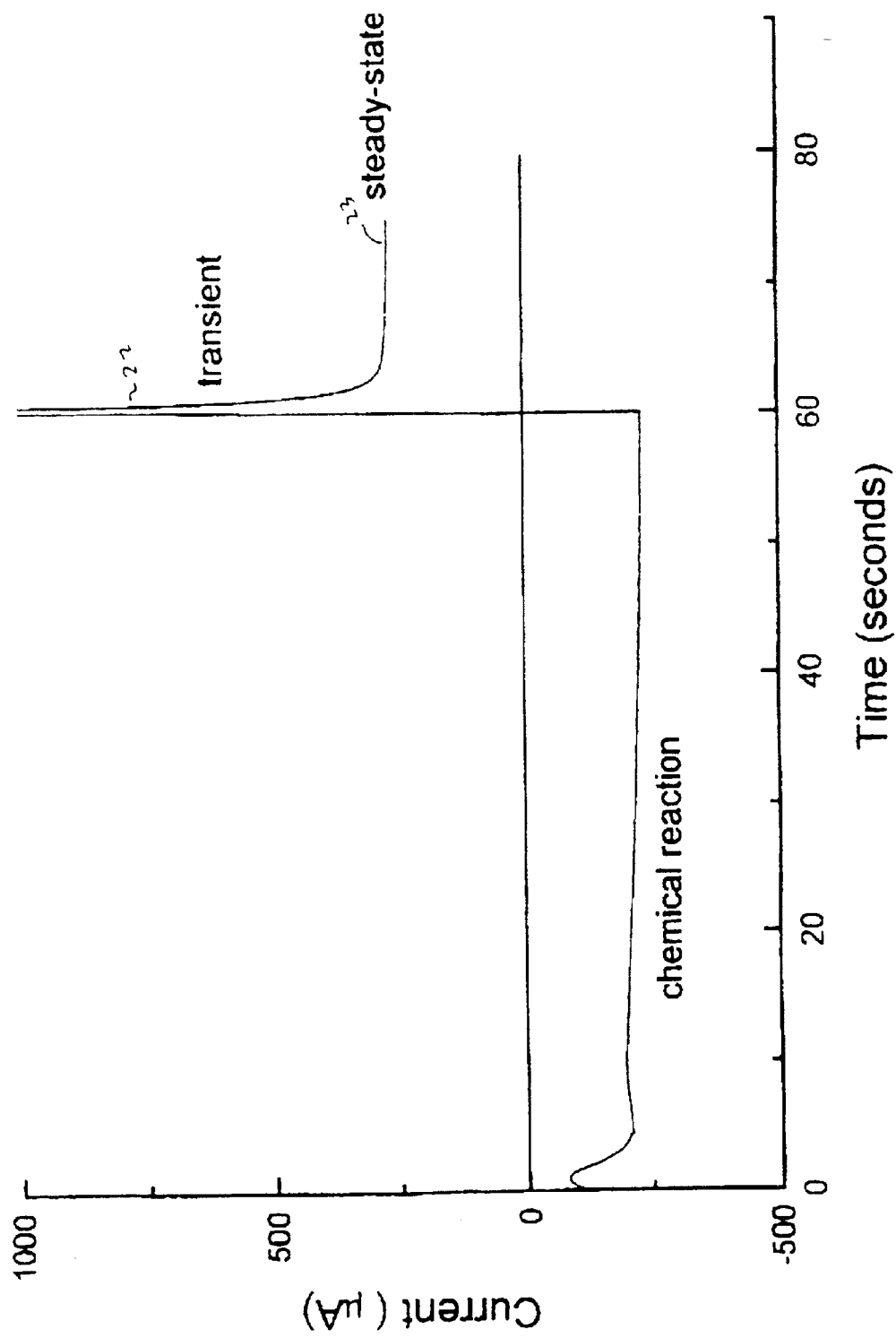
FIG. 11 shows the time dependence of current when an initial potential sufficient to oxidise hydrogen peroxide is applied.

If, during the period of enzyme reaction a potential is applied (FIG. 11) across the cell that is sufficient to oxidise hydrogen peroxide, then the following will happen during that period:

(a) glucose will be reacted to gluconic acid.
(b) ferrocyanide and hydrogen peroxide will result.
(c) the ferrocyanide/ferricyanide redox will eventually reach steady state.
(d) the peroxide will be oxidised at the anode and the electrons used to convert ferricyanide to ferrocyanide.

In total, after a period of time (approximately 2½ seconds in FIG. 11) at a constant potential all the peroxide will be converted to oxygen (which is then a catalyst, and will return to complete more enzyme chemistry until glucose is exhausted), and the electrons utilised to convert ferricyanide to ferrocyanide.

At this stage (60 seconds in FIG. 11) a reverse transient is applied. That is, the polarity of the cells is switched. but now at the lower potential suitable for the ferricyanide/ferrocyanide redox reaction. The final steady state ferrocyanide will once again reflect the initial glucose concentration. This can be analysed in the previously described manner to determine the total concentration of glucose in the initial sample.

Using the method of the preferred embodiments, the reaction phase of the test can be monitored in situ electrochemically without interfering with the measurement phase.

When the reaction is complete one can proceed to measurement without further delay.

The wait time will vary from test to test and will be the minimum necessary for any particular sample and cell, taking account of changes in enzyme activity from cell to cell as well as different temperatures and glucose concentrations. This is in stark contrast to prior art in which measurement is delayed until the maximum time required for reaction after allowing for all these factors.

In the present method the reaction phase is monitored by applying a potential between the two electrodes of, for example, −300 mV as soon as the cell begins to fill with sample.

A linear concentration profile of the reduced mediator is soon achieved across the cell. As more reduced mediator is produced by the enzyme reaction with glucose this linear concentration profile becomes steeper and the current increases. When the reaction is complete the current no longer increases. This point can be detected by well known electronic means and the measurement phase of the test can then be commenced.

The end-point of the reaction can also be estimated by fitting a theoretical kinetic equation to the current versus time curve generated during this part of the test.

This equation can predict the degree of completion of the reaction at any time. So would allow knowledge of when the end-point would occur without having to wait to get there.

This would further shorten the test time. For example, one could fit an equation to the measured prepulse current versus time curve. This equation could then predict that at time X the reaction will be, for example, 90% complete. If one measures the concentration at time X one would then divide the answer by 0.90 to get the true concentration.

The measurement of concentration in this system is done by reversing the potential, i.e. applying +300 mV between the electrodes. A current versus time curve will then occur, which is the same as that of the second transient in a double transient experiment le by transforming the current 1 measured during the measurement phase one can obtain a plot of $\ln(i/i_{ss}-1)$ versus time which will have a slope of $-4\text{ pi}^2 D/l^2$ and an intercept $\ln(4)$. The normal analysis can then be used to obtain the concentration of glucose.

In some situations it may be difficult or impossible to know the distance between the electrodes in the electrochemical cell. For example, very small separations (ca. 10 microns) may be very difficult to manufacture or measure reproducibly. In these situations the use of information from two adjoining cells can be used to calculate the concentration of an analyte in a sample without knowledge of the cell separation if one of the cells contains a known concentration of the analyte or the corresponding reduced mediator prior to sample addition. Alternatively, a known quantity of this analyte or reduced mediator can be added to the sample destined for one of the two cells prior to addition of the sample to the cell. Another variation is if both cells contain a pre-determined analyte or reduced mediator concentration but each has a different concentration. Yet another variation is if two different predetermined quantities of the analyte or reduced mediator are added to two aliquots of the sample, which are then added to the adjoining cells.

The two electrochemical cells are then used in the normal fashion, and from each cell the following quantities are measured: steady state current ($i_{ss}$) and the slope of the straight line defined by $\ln(i/i_{ss}-1)$ versus time, where i is the measured current. With a knowledge of these values and also a knowledge of the difference in concentration of the analyte or reduced mediator between the two cells, which is known (it is equal to that value purposely added to one cell), it is possible to calculate the concentration of analyte or reduced mediator in the sample, without any knowledge of the separation distance of the electrodes.

The above can be used in conjunction with a third cell that is used to measure the background current or concentration due to current caused by, for example, reduced mediator formed by the application and drying of the chemistry, catalytic effect of the metal surface, oxidation of the metal surface, sample components that have effects on the analyte or mediator, electrochemically responsive components of the sample etc. This background concentration or current would be subtracted from the values measured from the two cells discussed above to calculate the true values for each cell resulting from the analyte in the sample, and in one case also the analyte or reduced mediator purposely added to the cell or the sample.

As will be apparent to those skilled in the art, from the teaching hereof the method is suitable for use with automatic measuring apparatus. Cells of the kind described may be provided with electrical connectors to an apparatus provide with a microprocessor or other programmed electronic control and display circuits which are adapted to make the required measurements perform the required calculations and to display the result. The method may be used to measure the concentration of analytes other than glucose and in liquids other than blood.

The method may be conducted using cells of other design and/or construction and using known catalysts and redox systems other than that exemplified.

EXAMPLES OF HEATED STRIP EXPERIMENTS

Example 1

Figure 2:
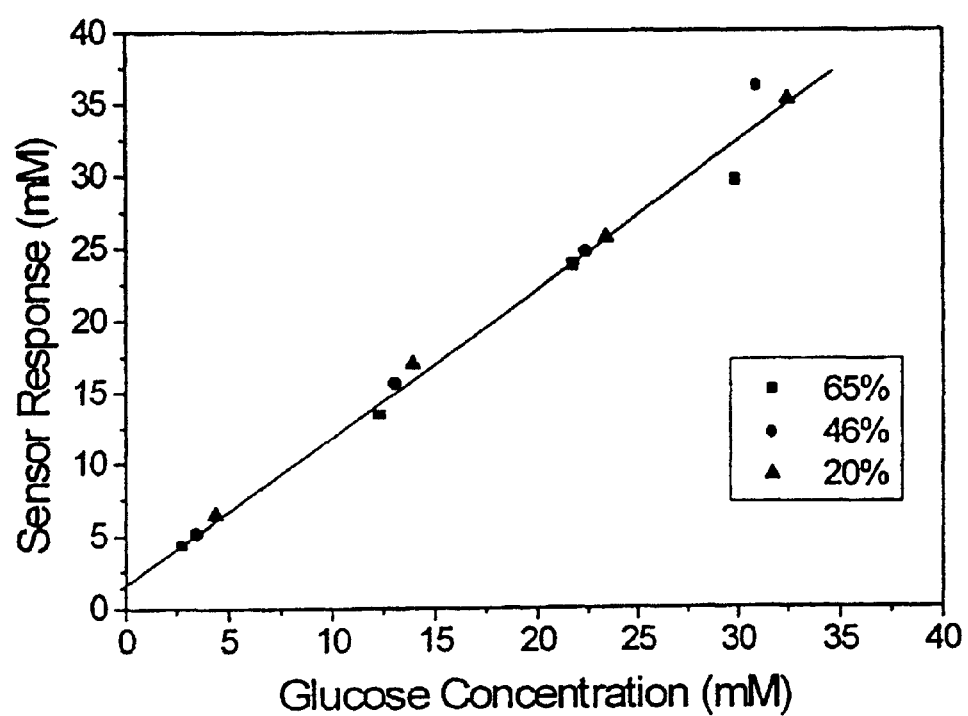
FIG. 2 shows the results of tests conducted in accordance with one embodiment of the present invention for blood samples with varying haematocrits and glucose concentrations.

Disposable test strips of the type described in PCT/AU96/00724 were heated by placing a metal bar, heated to 50° C., in contact with the sample receiving area of the strip. Whole blood samples were introduced into the sample receiving area of the strip and 13 seconds allowed for the glucose present in the sample to react with the sensor reagents. Current was then collected for ten seconds and analyzed according to the methods described in PCT/AU96/00723. The results of these tests for blood samples with haematocrits of 67.5%, 49.5% and 20% and glucose concentrations between 2.5 mM and 30 mM are shown in FIG. 2.

Example 2

Figure 3:
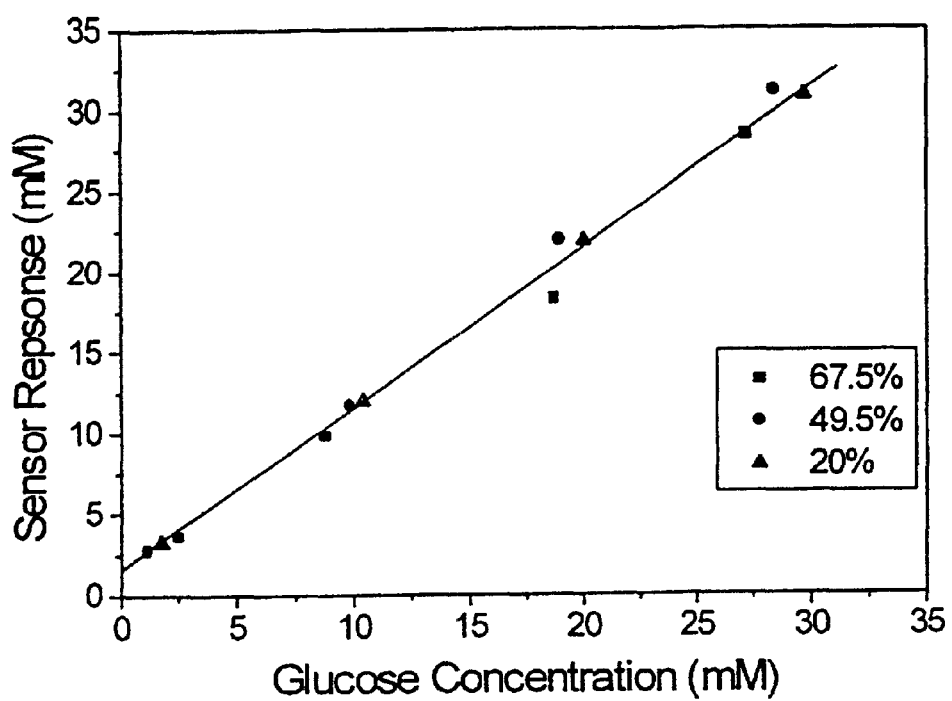
FIG. 3 shows the results of tests conducted in accordance with another embodiment of the present invention for blood samples with varying haematocrits and glucose concentrations.

Disposable test strips of the type described in PCT/AU96/00724 were modified by adhering a heater element to the base of the strip, beneath the sample receiving area. The heater element was fabricated by sputtering two parallel low resistance metallic tracks onto a polyester substrate and then sputtering a thin, resistive metallic track at right angles to the low resistance metallic tracks, such that the resistive metallic track contacted both of the parallel low resistance tracks. This heater was then glued to the base of the disposable test strip using an adhesive, such that the resistive track was positioned directly beneath and facing the sample receiving area on the strip. The parallel low resistance tracks protruded from the end of the strip and provided electrical contacts for a power supply to power the heater. The power supply for the heater consisted of a battery and a variable resistor, which could be adjusted to vary the rate of heating. Whole blood samples were introduced into the sample receiving area of the strip and 20 seconds allowed for the glucose present in the sample to react with the sensor reagents. Current was then collected for ten seconds and analyzed according to the methods described in PCT/AU96/00723. The results of these tests for blood samples with haematocrits of 65%, 46% and 20% and glucose concentrations between 2.8 mM and 32.5 mM are shown in FIG. 3.

Although the invention has been herein described with reference to electrochemical methods for measuring glucose concentration in blood it will be appreciated that the method may also be applied utilising suitable spectroscopic or other measuring methods and to samples other than blood and to analytes other than glucose.

What is claimed is:

1. An electrochemical cell, comprising a spacer pierced by an aperture which defines a cell wall, a first metal electrode on one side of the spacer extending over one side of the aperture, a second metal electrode on the other side of the spacer extending over the side of the aperture opposite the first electrode, means for admitting a sample to the cell volume defined between the electrodes and the cell wall, and means for heating a sample contained within the cell, wherein the means for heating the sample comprises an exothermic reaction produced upon contact of said sample with at least one suitable reagent, and wherein the at least one suitable reagent is a two component system which liberates heat upon mixing.

2. The electrochemical cell according to claim 1 wherein the means for heating a sample further comprises an electrically resistive element.

3. The electrochemical cell according to claim 1, further comprising means of measuring a concentration of an analyte or a concentration of a species representative thereof in a sample at a predetermined point on a reaction profile by means that are substantially independent of a temperature of the sample in the electrochemical cell.

4. The electrochemical cell according to claim 3, wherein the predetermined point on the reaction profile is a steady state.

5. The electrochemical cell according to claim 1, wherein the electrochemical cell comprises a mediator, wherein the mediator comprises a species representative of a concentration of an analyte.

6. The electrochemical cell according to claim 5, wherein the mediator is an enzyme mediator.

7. The electrochemical cell according to claim 1, wherein the at least one suitable reagent is a salt which liberates heat on dissolution.

8. The electrochemical cell according to claim 7, wherein the salt is selected from the group consisting of aluminum chloride, lithium halides, lithium sulfate, magnesium halides, and magnesium sulfate.

9. The electrochemical cell according to claim 1, wherein each of the two components are placed in separate locations in the electrochemical cell.

10. The electrochemical cell according to claim 9, wherein said two components are placed as coatings upon opposite internal cell walls of the electrochemical cell.

11. The electrochemical cell according to claim 1, wherein the means for heating a sample further comprises an electrical heater.

12. The electrochemical cell according to claim 11, wherein said means for heating a sample is a current applied to resistive elements associated with said measuring means.

13. The electrochemical cell according to claim 1, wherein the means for heating a sample is capable of raising a sample temperature by from 5 to 15° C.

14. The electrochemical cell according to claim 1, wherein the means for heating a sample is capable of raising a sample temperature to a final sample temperature within a period of 2–10 seconds.

15. The electrochemical cell according to claim 1, wherein the means for heating the sample is capable of achieving a peak sample temperature within 2–5 seconds.

16. The electrochemical cell according to claim 1, wherein the electrochemical cell comprises a glucose sensor.

17. The electrochemical cell according to claim 1, wherein the electrochemical cell comprises a glucose sensor capable of measuring a concentration of glucose in a blood sample.

18. The electrochemical cell according to claim 1, further comprising an enzyme.

19. The electrochemical cell according to claim 18, wherein the enzyme comprises glucose dehydrogenase.

20. The electrochemical cell according to claim 18, further comprising an oxidizing mediator.

21. The electrochemical cell according to claim 20, wherein the oxidizing mediator comprises ferricyanide.

22. The electrochemical cell according to claim 1, wherein the means for heating the sample further comprises a resistive element.

23. The electrochemical cell according to claim 22, further comprising means of applying a potential across the resistive element to generate an amount of heat.

24. The electrochemical cell according to claim 23, further comprising means of interrupting the potential across the resistive element and applying a potential between the first electrode and second electrode to perform the electrochemical assay of the analyte.

25. The electrochemical cell according to claim 23, wherein the means of applying a potential across the resistive element is capable of maintaining the potential during an assay of an analyte at an initial level or at a lower level sufficient to substantially maintain a sample temperature of a desired level.

26. The electrochemical cell according to claim 23, wherein the means for applying potential to the resistive element is capable of measuring a current flowing through the resistive element and automatically adjusting the potential so as to maintain a required power output.

27. The electrochemical cell according to claim 26, wherein the power output is capable of being adjusted on a basis of an ambient temperature measured by a separate sensor.

* * * * *